United States Patent [19]
Endo

[11] Patent Number: 5,378,466
[45] Date of Patent: Jan. 3, 1995

[54] THERAPEUTIC AGENT FOR ALLERGIC DISEASES

[75] Inventor: Koichi Endo, Tokushima, Japan

[73] Assignee: Bio Cell Matelia Co., Ltd., Sapporo, Japan

[21] Appl. No.: 925,466

[22] Filed: Aug. 4, 1992

[30] Foreign Application Priority Data

Aug. 6, 1991 [JP] Japan .................................. 3-222041

[51] Int. Cl.$^6$ ............................................. A61K 35/78
[52] U.S. Cl. ................... 424/195.1; 514/969; 514/885; 514/861; 514/864; 514/826
[58] Field of Search ............ 424/195.1; 514/969, 514/885, 861, 864, 826

[56] References Cited

U.S. PATENT DOCUMENTS 4,702,923 10/1987 Tokumaru .............................. 426/61
4,797,290 1/1989 Tokumaru et al. .................... 426/43

OTHER PUBLICATIONS

The Pharmaceutical Features of Acarthoparer Senticosus, Jap. Translation of Extract of Siberian Branch Soviet Academy Publication–I. I. Brefman, I. V. Duldimof.

Primary Examiner—John W. Rollins
Assistant Examiner—Howard C. Lee
Attorney, Agent, or Firm—Peter Jon Gluck; Vineet Kohli; Thomas R. Morrison

[57] ABSTRACT

A therapeutic agent for allergic diseases containing as an active ingredient an extract of *Acanthopanax senticosus Harms*. It became possible to provide a medicine enabling allergic diseases to be treated without causing almost no side effects.

4 Claims, 1 Drawing Sheet

THERAPEUTIC AGENT FOR ALLERGIC DISEASES

BACKGROUND OF THE INVENTION

The therapeutic agent for allergic diseases of the present invention can be applied to treatment of various allergic diseases such as atopic dermatitis and asthma.

PRIOR ARTS

In recent years, the number of patients with various allergic diseases such as atopic dermatitis and pollinosis has increased and their treatment has become a social problem. At present, however, symptomatic treatments are relied on heavily in treating them and, despite the fact that superior therapeutic agents leading to radical treatment of allergic diseases are desired earnestly, we cannot but say that development of such agents is at the stage of groping in the dark. Although various new antiallergic agents have recently been developed, none of them can give doctors satisfaction because all of them are inferior in their quality. Antihistamic agents and bronchodilators are still mainly used for treatment of allergic diseases, and the therapeutic effects of these types of symptomatic treatment agents have their limit although some of them have high potency and minimal side effects. Although adrenocortical hormonal formulations are used in difficultly cured cases, they are also for symptomatic treatment and should not be used widely because patients often suffer from their severe side effects.

SUMMARY OF THE INVENTION

The object of the present invention is to provide a therapeutic agent for allergic diseases which enables radical treatment of allergic diseases and has minimal side effects.

The therapeutic agent for allergic diseases of the present invention contains as an active ingredient an extract of acanthopanax senticosus Hams.

DETAILED DESCRIPTION OF THE INVENTION

Figure 1:
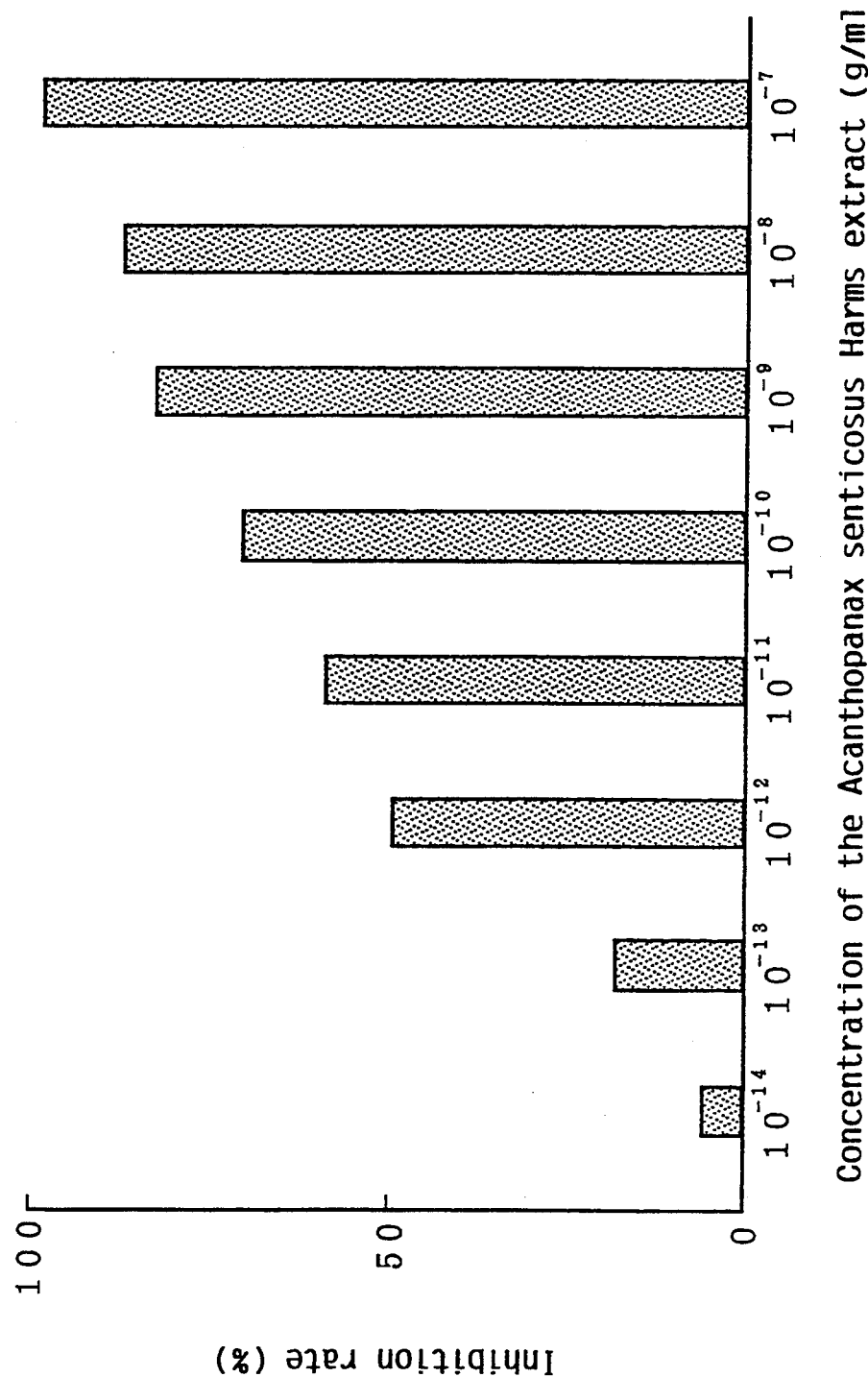
FIG. 1 shows the relation between the concentration of an *Acanthopanax senticosus Harms* extract and the inhibition rate of histamine release.

*Acanthopanax senticosus Harms* is a plant belonging to Araliaceae similarly to ginseng and is known as a folk medicinal herb in Hokkaido. Its known medical effects include a sthenic, calmative effect, a hypoglycemic effect, an antihypertensive effect and a tumor growth inhibiting effect. Its toxicity is low and the $LD_{50}$ of its root has been reported to be 31 g per 1 kg body weight of mice (I. I. Brefman, I. V. Duldimof, the Siberia branch of Soviet Academy). The inventors, after further researches on the pharmacological effect of *Acanthopanax senticosus Harms*, found that it has a superior therapeutic effect on allergic diseases although its functional mechanism is not clear.

The medicinal part of *Acanthopanax senticosus Harms* is its stalk, root or leaf and *Acanthopanax senticosus Harms* extracts can be obtained by treating these parts by various publicly known methods. For instance, an *Acanthopanax senticosus Harms* extract can be obtained by the following method.

(Preparation of an *Acanthopanax senticosus Harms* extract)

After 100 kg of dried *Acanthopanax senticosus Harms* is put in an extractor, 4 times by weight of a warm solvent for extraction (50% ethanol at a temperature of 70° C. or below) is added to the extractor and the mixture is allowed to stand for two days.

The liquid extract and the residue are separated from each other by a centrifuge.

Three times by weight of the above warm solvent for extraction is added to the residue and the mixture is allowed to stand for one day.

A liquid extract, which is obtained by centrifugation of the mixture, is mixed with the previous mixture to make a mixed liquid extract.

After the mixed liquid extract is filtered while being maintained at 50° C., the resulting filtrate is further filtered until a filtrate transparent at normal temperature is obtained.

The resulting final filtrate is distilled at a temperature of 85° C. or below at a pressure of 720 mmHg to distill ethanol off.

After the resulting solution is filtered, the filtrate is concentrated under reduced pressure to produce a low consistency extract with a water content of 50%.

Although the above low consistency extract can be stored as it is, it is preferably subjected to the following treatment to make a transparent extract (fluid extract) which can easily be used.

Seven kg of distilled water and 400 g of ethanol were added to 1 kg of the low consistency extract to make a liquid mixture.

After the liquid mixture is allowed to stand for a long period to precipitate insoluble matters, ethanol is distilled off until the ethanol content becomes 0.32%.

The resulting liquid is filtered to produce a transparent extract (fluid extract).

First of all, the inventors made an experiment wherein the in vitro antiallergic effect of the thus obtained Acanthopanax senticosus Harms extract was determined.

Experimental Example 1

After rats weighing 200 to 300 g were killed by letting their blood out, abdominal section was performed of the dead rats and mast cells in their abdominal cavities were collected; mast cells are cells inducing an allergic reaction.

After the mast cells were suspended in a liquid culture medium and the liquid suspension was poured into 10 test tubes, various concentrations of the *Acanthopanax senticosus Harms* extract were added to test tubes while maintaining them at 37° C. Five minutes later, an allergic reaction was induced by adding anti-rat IgE serum to each test tube. Then, after maintaining the test tube at 37° C. for 10 minutes, the content of the test tube was centrifuged and the amount of free histamine in the supernatant was measured. The amount of free histamine represents the intensity of an allergic reaction. The quantitative determination of histamine was performed by a usual method using a spectrophotofluorometer.

The results of the experiment are shown in FIG. 1. The concentration (as a dry extract) of the *Acanthopanax senticosus Harms* extract is plotted as abscissa and the inhibitive effect on histamine release (namely, inhibitive effect on an allergic reaction) as ordinate. The 0% inhibition rate indicates the absence of any inhibitive effect and the 100% inhibition rate indicates that an allergic reaction within the test tube was completely inhibited. The data shown in this figure are averages each of five experimental results. The *Acanthopanax senticosus Harms* extract exhibited a 100% inhibitive effect at a concentration of $10^{-7}$ g/ml and a 50% inhibitive effect at a concentration of $10^{-2}$ g/ml. The concentration of $10^{-2}$ g/ml represents one resulting from dissolving 1 mg of a dry extract of *Acanthopanax senticosus Harms* in 1,000 tons of water. It is seen from the fact that such a low concentration of the Acanthopanax senticosus Harms extract inhibits the intensity of an allergic reaction within a test tube to ½ that the *Acanthopanax senticosus Harms* extract has a very strong antiallergic effect. In this connection, sodium cromoglicate, a currently most widely used antiallergic agent, only exhibited an inhibition rate of 20% at a concentration of $10^{-5}$ g/ml, an inhibition rate of 35% at a concentration of $10^{-4}$ g/ml and an inhibition rate of 51% at a concentration of $10^{-3}$ g/ml. Tranilast exhibited an inhibition rate of 18% at a concentration of $10^{-4}$ g/ml. Thus it is seen that the *Acanthopanax senticosus Harms* extract of the present invention has a very strong antiallergic effect.

Experimental Example 2

The following experiment was made in order to investigate the inhibitive effect of the *Acanthopanax senticosus Harms* extract on the configurational change of mast cells caused by an allergic reaction.

Mast cells were collected from the abdominal cavities of rats and were suspended in a liquid culture medium before the suspension was poured into three test tubes. Then the test tubes were treated in the following manner.

Test tube 1: It was maintained at 37° C. for 15 minutes without any addition.

Test tube 2: After it was maintained at 37° C. for five minutes without any addition, an allergic reaction was induced by adding anti-rat IgE serum and then the test tube was maintained at 37° C. for ten minutes.

Test tube 3: After a $10^{-7}$ g/ml concentration (as a dry extract) of the *Acanthopanax senticosus Harms* extract was added to the test tube and it was maintained at 37° C. for five minutes, an allergic reaction was induced by adding anti-rat IgE serum and then the test tube was maintained at 37° C. for ten minutes.

Following that, formalin and toluidine blue were added to all the test tubes to fix and stain mast cells before they were microscopically observed.

Although mast cells in test tube 1 were nodal itself, in test tube 2, in which a strong allergic reaction was induced, the contents of mast cells scattered around and a marked change was observed. On the other hand, mast cells in test tube 3 to which the *Acanthopanax senticosus Harms* extract had been added kept a normal configuration similarly to mast cells in test tube 1 despite the fact that an allergic reaction was induced in the same manner as for test tube 2. It is seen from this experiment that the *Acanthopanax senticosus Harms* extract significantly inhibit an allergic reaction.

Furthermore, the effect of the *Acanthopanax senticosus Harms* extract was investigated by getting persons with allergic disease to take or apply the extract according to their symptoms. In examples, the *Acanthopanax senticosus Harms* extract refers to the above fluid extract and an ointment containing the *Acanthopanax senticosus Harms* extract refers to one prepared by mixing 1 kg of a base (Cinderella Base, a product of Shinsei Yakuhin Kogyo Co., Ltd.) with 0.3% of the *Acanthopanax senticosus Harms* extract before the mixture is heated to 90° C. to achieve dissolution, followed by cooling the dissolved mixture to ordinary temperature (30° C.) before the cooled mixture is agitated by a mixer to make it homogeneous.

EXAMPLE 1

A male university student aged 20. He had systemic atopic dermatitis. He took 15 drops of the *Acanthopanax senticosus Harms* extract once daily for nine days, and from the 10th day he took 7 drops of it three times daily. He was completely cured in about 6 months.

EXAMPLE 2

A baby girl aged six months. She had allergic constitution from her birth. Although an ointment for antipruritic was applied to her, itching did not disappear and she continued to cry at night because of itching. She was given two drops of the *Acanthopanax senticosus Harms* extract contained in warm water in a sake cup in the morning and evening and as a result she stopped crying at night from the second day. She was given two drops of the extract contained in warm water in a sake cup once daily from one month after the start of medication and was completely cured three months after the start of medication.

EXAMPLE 3

A female aged 26. She had systemic allergy. When she took five drops of the *Acanthopanax senticosus Harms* extract three times daily, a nervous feeling and itching disappeared in one week. She is continuing to take the extract for improvement of her constitution.

EXAMPLE 4

A female aged 23. She had systemic atopic dermatitis and a fluid came out from her face. The symptom was not improved despite the fact that she went to hospital regularly and the symptom did not take a favorite turn although she took a herb medicine for six months. She took 15 drops of the *Acanthopanax senticosus Harms* extract once daily. As a result, a thin film was formed in three days, and the scab disappeared and her skin became clean in seven days. She stopped taking the extract three months after the start of taking it.

EXAMPLE 5

A boy aged 5. He repeatedly had an impetigo-like symptom. The symptom was not readily improved despite the fact that he went to hospital regularly. Five to six drops of the *Acanthopanax senticosus Harms* extract were sublingually administered to him two times daily and as a result he was completely cured in about one month. There was no relapse.

EXAMPLE 6

A girl aged 17. She had atopic dermatitis. When she both took and applied the *Acanthopanax senticosus Harms* extract, itching was gone soon and the redness of her skin became faint in one month (when 30 ml of the extract had been used). She is taking the extract even now.

EXAMPLE 7

A female aged 46. She had mammary cancer, and had soybean allergy from using soybean nucleic acid. When she used 15 drops of the *Acanthopanax senticosus Harms* extract three times daily, her symptom was alleviated in two days. She is now using 10 drops of the extract in the morning and evening in order to prevent relapse.

EXAMPLE 8

Contact dermatitis. A male nurse for a hospital for old people came to have contact dermatitis because of his work. Although he applied a usual ointment, his symptom was not improved. Etching was gone when he applied a three-fold dilution in tepid water of the *Acanthopanax senticosus Harms* extract. He is using the extract even now.

EXAMPLE 9

A female aged 50. She had allergic rhinitis. When one drop of the *Acanthopanax senticosus Harms* extract was instilled into each of the right and the left nasal foramens, rhinorrhea stopped coming out in ten minutes. During relapse, the same effect was achieved by a threefold dilution of the extract.

EXAMPLE 10

A female aged 47. She had asthma. Although 10 drops of the *Acanthopanax senticosus Harms* extract were administered to her three times daily, her symptom did not take a favorite turn. The dose of the extract was increased to 15 drops per time from the second week and, as a result, the frequency of coughing decreased in four days. After that, the dose was gradually reduced and she stopped using the extract about three months after the start of medication.

EXAMPLE 11

A girl aged 16. She had asthma. She stopped having a fit after 15 drops of the *Acanthopanax senticosus Harms* extract were sublingually administered to her once. For a portion of medicine to be taken only once during a fit.

EXAMPLE 12

A boy who was a second-year student of a junior high school. He was a patient with asthma having been hospitalized once a month. When he used 5 drops of the *Acanthopanax senticosus Harms* extract three times daily, one week later his symptom was alleviated to such an extent that he did not have to be hospitalized even when he had a fit. One month later, he recovered from illness to such an extent that he only had a light fit when he had an immoderate exercise. He was nearly completely cured six months after the start of using the extract.

EXAMPLE 13

A boy aged 5. He had asthma. He had one or two fits in a month on the average and had been hospitalized for about one week for one fit. When three drops of the *Acanthopanax senticosus Harms* extract were administered to him in the morning and evening, one week later his symptom was alleviated to such an extent that he did not have to be hospitalized even when he had a fit. He became free from bed-wetting in about one month and came to have no fits in about five months. He is taking the extract even now for a prophylactic treatment.

EXAMPLE 14

A female aged 42. She had the history of having asthma for five years. As she had a violent fit of coughing when she lay on a bed to sleep, she repeatedly had a nap on a sofa. As she developed dyspnea during a fit, she used an oxygen inhaler to alleviated the symptom. When 15 drops of the *Acanthopanax senticosus Harms* extract were sublingually administered to her three times daily, the violent fit of coughing was alleviated in one week and she was almost completely cured in six months.

EXAMPLE 15

A boy who was a fourth,-grade pupil of an elementary school. He had bronchial asthma. He had two or three fits in a month and had been hospitalized on all such occasions. As he coughed violently and had dyspnea of such a degree that a whistling sound comes out during breathing, five drops of the *Acanthopanax senticosus Harms* extract were administered to him and as a result his cough calmed down in several minutes. After that, five drops of the extract were administered to him three times daily and, as a result, the frequency of fits decreased and he became free from hospitalization. He was nearly completely cured when he had used 90 ml of the extract.

EXAMPLE 16

A boy aged 3. He had asthma. When he took two drops of the *Acanthopanax senticosus Harms* extract in the morning and evening, his fits disappeared in about one month. He is taking the extract now for a prophylactic treatment,

EXAMPLE 17

A male aged 70. As he woke up because of an asthma fit every morning, he took 1 ml of the *Acanthopanax senticosus Harms* extract before going to bed. As a result, he did not have any asthma fit from the next morning.

EXAMPLE 18

A male in his forties. He had been hospitalized because of a very strong degree of asthma. When he drank 1 ml of the *Acanthopanax senticosus Harms* extract during a fit, severe coughs calmed down. His symptom was alleviated after taking the extract for two weeks.

EXAMPLE 19

A physician aged 81. He had 50 and several fits of coughing in a day and was in a state of dyspnea. Although he used various kinds of medicines because of the professional character, his health did not take a favorite turn and he had suffered from illness for ten years. When he took 10 drops of the *Acanthopanax senticosus Harms* extract two times daily, the symptom was alleviated to about 60% about one month after the start of using the extract. From the second month he used 8 drops of the extract three times daily and, as a result, the degree of improvement became rapid, coughs and phlegm came to be easily loosened and the frequency of coughing became about one tenth. After that, he continued to use the extract and was completely cured six months after the start of medication.

EXAMPLE 20

A baby aged 8 months. He had atopic dermatitis from his birth and had systemic rash and tuber sore. As the symptoms were aggravated still more even when an ointment received from a hospital was applied, use of the ointment was stopped. When an ointment containing the *Acanthopanax senticosus Harms* extract was applied to the body, the redness became lighter in the next morning. His symptoms were gradually improved by applying the ointment about three times daily. His skin became clean in about one month and now the ointment is occasionally used.

EXAMPLE 21

A female aged 23. She had atopic dermatitis. Eczema appeared in an area extending from her neck to her face and, because of makeup, her face had eruption and it was aggravated. Her symptom was not improved even when she used a steroidal ointment received from a hospital. After that when she used an ointment containing the *Acanthopanax senticosus Harms* extract, eczema disappeared on the third day of using the ointment and the redness disappeared in about one week. She could use cosmetics about one month after the start of using the ointment.

EXAMPLE 22

A female aged 62. As she had large spots on her hands and face, she applied an ointment containing the *Acanthopanax senticosus Harms* extract to the spots in the morning and evening. As a result, one week later the color of the spots became almost same as that of her skin.

EXAMPLE 23

A male aged 20. When he did a construction work as a part-time job, his face got sunburnt and spots appeared on it. Therefore, he applied an ointment containing the *Acanthopanax senticosus Harms* extract to the spots. As a result, his face was restored to the former state in about one week.

EXAMPLE 24

An infant aged 6. He felt itchy because of atopic dermatitis and a fluid was always coming out. When an ointment containing the *Acanthopanax senticosus Harms* extract was applied to his skin, itching disappeared in about 10 minutes and formation of a thin film was observed in the next morning. On the tenth day, his skin was clear without any scab and scar.

As described above, the *Acanthopanax senticosus Harms* extract of the present invention had a superior therapeutic effect on various allergic diseases. Although the standard dose of the fluid extract is 0.5 ml per time for adults and can be changed according to symptom, about 0.5 to 3 ml per day of the fluid extract was administered.

Although only the extract and the ointment were experimentally used this time, the extract can also be used in a powder, granules, tablets, pills, capsules, troches, a tincture, a syrup, an ophthalmic liquid preparation, an injection, an emulsion, a paste, a cataplasm, a liniment, a lotion, an eye ointment, suppositories, an aerosol and the like.

Because of the present invention, it became possible to provide a medicine enabling allergic diseases to be treated without causing almost no side effects.

What is claimed is:

1. A pharmaceutical composition for treating allergic diseases comprising:
    a fluid extract;
    said extract containing from about $10^{-14}$ g/ml to about $10^{-7}$ g/ml of *Acanthopanax senticosus Harms.*, as active ingredient;
    said extract being extracted from dried leaves of *Acanthopanx senticosus Harms.*, with aqueous ethanol at a temperature exceeding ambient temperature; and
    a pharmaceutically acceptable carrier.

2. The pharmaceutical composition of claim 1, wherein said pharmaceutical composition is extracted with aqueous ethanol.

3. A method for treating allergic diseases, comprising:
    extracting an extract from dried leaves of *Acanthopanx senticosus Harms.*, with aqueous ethanol at a temperature exceeding ambient temperature; and,
    applying a pharmaceutical composition comprising said extract of *Acanthopanx senticosus Harms.*, and a pharmaceutically acceptable carrier, in fluid extract form, at a dosage level of from about 0.5 ml to about 3 ml per day to persons with allergic diseases.

4. A product, produced by the method of claim 3, wherein said pharmaceutical composition is in fluid extract form.

* * * * *